(12) United States Patent
Cheng et al.

(10) Patent No.: US 9,763,805 B2
(45) Date of Patent: Sep. 19, 2017

(54) SPACER WITH TEMPORARY FIXATION PLATE

(71) Applicant: Alphatec Spine, Inc., Carlsbad, CA (US)

(72) Inventors: Yang Cheng, Foothill Ranch, CA (US); Jonathan T. Costabile, San Diego, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 0 days.

(21) Appl. No.: 15/283,760

(22) Filed: Oct. 3, 2016

(65) Prior Publication Data

US 2017/0020680 A1 Jan. 26, 2017

Related U.S. Application Data

(62) Division of application No. 14/634,107, filed on Feb. 27, 2015, now Pat. No. 9,603,718.

(60) Provisional application No. 62/117,384, filed on Feb. 17, 2015, provisional application No. 61/945,314, filed on Feb. 27, 2014.

(51) Int. Cl.
*A61F 2/44* (2006.01)
*A61B 17/70* (2006.01)
*A61B 17/86* (2006.01)
*A61F 2/30* (2006.01)

(52) U.S. Cl.
CPC .......... *A61F 2/447* (2013.01); *A61B 17/7059* (2013.01); *A61B 17/8625* (2013.01); *A61F 2/446* (2013.01); *A61F 2/4455* (2013.01); *A61F 2/4465* (2013.01); *A61F 2002/30672* (2013.01); *A61F 2002/4435* (2013.01); *A61F 2002/4475* (2013.01); *A61F 2220/0016* (2013.01); *A61F 2220/0041* (2013.01)

(58) Field of Classification Search
CPC ............. A61F 2/447; A61F 2002/4435; A61B 17/7059; A61B 17/8625
See application file for complete search history.

(56) References Cited

U.S. PATENT DOCUMENTS 5,928,061 A * 7/1999 Niino ...................... B24B 47/12
451/14
7,887,595 B1 * 2/2011 Pimenta .................. A61F 2/447
606/249

(Continued)

*Primary Examiner* — Ellen C Hammond
*Assistant Examiner* — Stuart S Bray
(74) *Attorney, Agent, or Firm* — Dinsmore & Shohl LLP

(57) ABSTRACT

A system for spinal fusion includes a spacer, a plate, an attachment member, and a first temporary fixation screw. The spacer includes a first coupling aperture having a first thread with a thread pitch that is greater than or equal to one third of a depth of the first coupling aperture. The plate includes a first attachment aperture and second coupling aperture. The attachment member includes a mating thread that mates with the first thread. The attachment member is configured to couple the spacer and the plate when inserted through the second coupling aperture and rotated to engage the first thread of the first coupling aperture. The first temporary fixation screw is configured to attach the plate to a first vertebra when inserted through the first attachment aperture and driven into the first vertebra.

11 Claims, 8 Drawing Sheets

(56) References Cited

U.S. PATENT DOCUMENTS

| | | | |
|---|---|---|---|
| 2004/0037915 A1* | 2/2004 | Dantlgraber | B29C 45/4005 425/589 |
| 2004/0053327 A1* | 3/2004 | Muller | G01N 21/6452 435/7.1 |
| 2004/0210218 A1* | 10/2004 | Dixon | A61B 17/7059 623/16.11 |
| 2005/0141983 A1* | 6/2005 | Fujii | F16B 33/02 411/308 |
| 2009/0210064 A1* | 8/2009 | Lechmann | A61B 17/86 623/17.16 |
| 2011/0190892 A1* | 8/2011 | Kirschman | A61F 2/44 623/17.16 |
| 2013/0060337 A1* | 3/2013 | Petersheim | A61F 2/447 623/17.16 |
| 2013/0178872 A1* | 7/2013 | Shriver | A61B 17/0057 606/148 |
| 2013/0238095 A1* | 9/2013 | Pavento | A61B 17/7059 623/17.16 |
| 2013/0345813 A1* | 12/2013 | Frank | A61F 2/447 623/17.16 |
| 2014/0012380 A1* | 1/2014 | Laurence | A61F 2/4465 623/17.16 |
| 2014/0046447 A1* | 2/2014 | Dunworth | A61F 2/447 623/17.16 |
| 2014/0277471 A1* | 9/2014 | Gray | A61F 2/442 623/17.15 |
| 2014/0277497 A1* | 9/2014 | Bennett | A61F 2/4455 623/17.16 |
| 2015/0005879 A1* | 1/2015 | Georges | A61F 2/447 623/17.11 |
| 2015/0025635 A1* | 1/2015 | Laubert | A61F 2/447 623/17.16 |
| 2015/0057754 A1* | 2/2015 | Reed | A61F 2/4611 623/17.16 |
| 2015/0238327 A1* | 8/2015 | Cheng | A61F 2/4611 623/17.16 |
| 2015/0328005 A1* | 11/2015 | Padovani | A61F 2/442 623/17.13 |
| 2015/0328007 A1* | 11/2015 | Padovani | A61F 2/447 623/17.13 |
| 2015/0328009 A1* | 11/2015 | Zappacosta | A61F 2/4455 623/17.16 |
| 2015/0328010 A1* | 11/2015 | Martynova | A61F 2/447 623/17.16 |
| 2016/0007983 A1* | 1/2016 | Frey | A61B 17/56 623/17.16 |
| 2016/0015523 A1* | 1/2016 | Lewis | A61F 2/447 623/17.16 |
| 2016/0045326 A1* | 2/2016 | Hansen | A61F 2/447 623/17.16 |
| 2016/0058480 A1* | 3/2016 | Laubert | A61F 2/447 606/289 |
| 2016/0067053 A1* | 3/2016 | Pisharodi | A61F 2/447 623/17.16 |

* cited by examiner

SPACER WITH TEMPORARY FIXATION PLATE

CROSS-REFERENCE TO RELATED APPLICATIONS

This application is a divisional of U.S. patent application Ser. No. 14/634,107 filed Feb. 27, 2015, which claims priority to U.S. Provisional App. Ser. No. 61/945,314, filed Feb. 27, 2014, and entitled "Systems and Methods for Insertion of Spinal Implants," incorporated by reference in its entirety herein. U.S. patent application Ser. No. 14/634,107 also claims priority to U.S. Provisional App. Ser. No. 62/117,384, filed Feb. 17, 2015, and entitled "Lateral Spacer with Temporary Fixation Plate," incorporated by reference in its entirety herein.

FIELD

The invention generally relates to spinal surgery and more particularly to interbody spacers with temporary fixation plates.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature.

Generally the correct curvature is obtained by manipulating the vertebrae into their proper position and securing that position with a rigid system of screws, rods, intervertebral spaces, and/or plates. The various components of the system may be surgically inserted through open or minimally invasive surgeries. The components may also be inserted through various approaches to the spine including anterior lateral, and posterior approaches and others in between.

Spinal fixation systems may be used in surgery to align, adjust, and/or fix portions of the spinal column, i.e., vertebrae, in a desired spatial relationship relative to each other. Many spinal fixation systems employ a spinal rod for supporting the spine and for properly positioning components of the spine for various treatment purposes. Vertebral anchors, comprising pins, bolts, screws, and hooks, engage the vertebrae and connect the supporting rod to different vertebrae. The size, length, and shape of the cylindrical rod depend on the size, number, and position of the vertebrae to be held in a desired spatial relationship relative to each other by the apparatus.

In a lateral spinal procedure, the patient may be placed first on his/her side. A spacer/cage/interbody may be inserted into the disc space between adjacent vertebrae after removing some or the entire disc. The patient must then be rotated to his/her back or his/her front in order to install additional fixation structures such as screws and rods and/or plates. However, while the patient is being rotated, the spacer may migrate anteriorly or posteriorly. This migration may disrupt adjacent tissues such as portions of the vascular system or the nervous system. The damage caused by such migration may jeopardize patient recovery and could even cause paralysis, severe blood loss, or other irreversible damage. Accordingly, the present invention includes one or more features to enable temporary fixation of the spacer while the patient is rotated into position for attachment of fixation structures.

SUMMARY

A system for spinal fusion includes a spacer, a plate, an attachment member, and a first temporary fixation screw. The spacer includes a first coupling aperture having a first thread with a thread pitch that is greater than or equal to one third of a depth of the first coupling aperture. The plate includes a first attachment aperture and second coupling aperture. The attachment member includes a mating thread that mates with the first thread. The attachment member is configured to couple the spacer and the plate when inserted through the second coupling aperture and rotated to engage the first thread of the first coupling aperture. The first temporary fixation screw is configured to attach the plate to a first vertebra when inserted through the first attachment aperture and driven into the first vertebra.

In other features, the thread pitch is greater than or equal to the depth of the first coupling aperture of the spacer. In still other features, the thread pitch is greater than or equal to two times the depth of the first coupling aperture of the spacer.

In other features, the first composing aperture includes a second thread with a second thread pitch equal to the first thread pitch.

In other features, the first thread includes a long lead trapezoidal form thread.

In yet other features, one half rotation of the attachment member engages less than one full thread of the first thread with the first coupling aperture to couple the spacer with the plate.

In still other features, the plate includes a pair of projections extending distally in a fork formation to engage with a pair of recessed portions of the spacer. The spacer further includes a distal end for insertion between two vertebrae, a middle section including a pair of recessed portions on an outer surface of the middle section, and a proximal end including the coupling aperture.

In other features, the plate includes a second attachment aperture. The system further includes a second temporary fixation screw configured to attach the plate to a second vertebra when inserted through the second attachment aperture and driven into the second vertebra.

DETAILED DESCRIPTION

Figure 1:
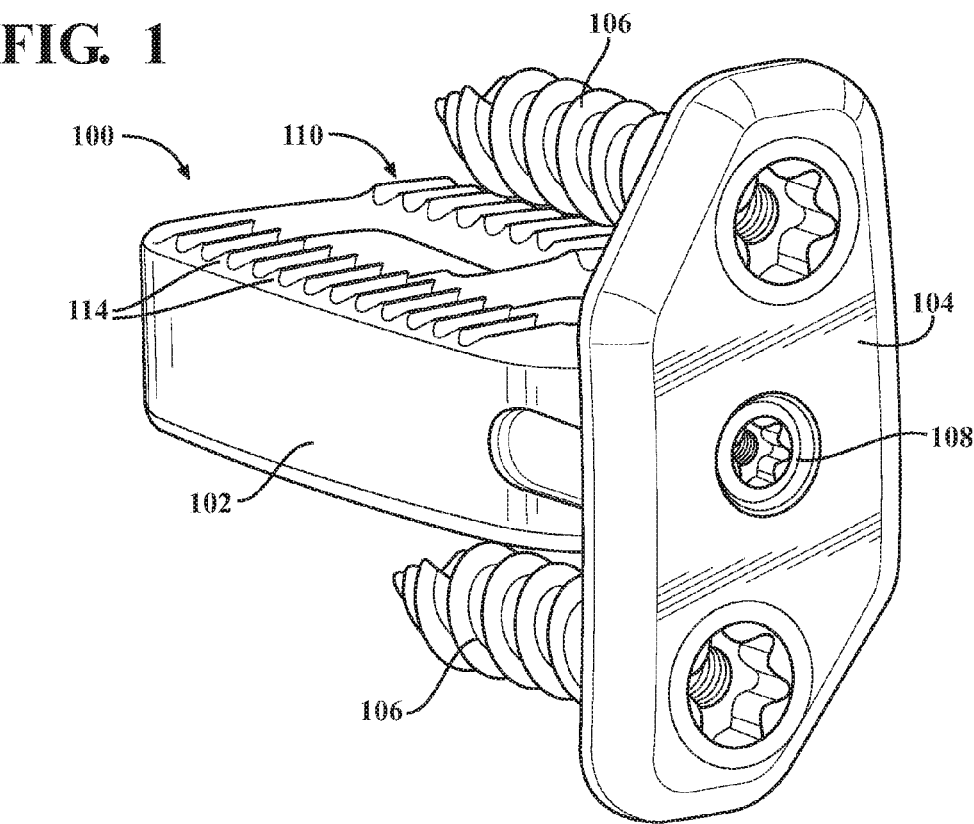
FIG. 1 is a perspective view of an exemplary implant according to the principles of the present disclosure.
Figure 2:
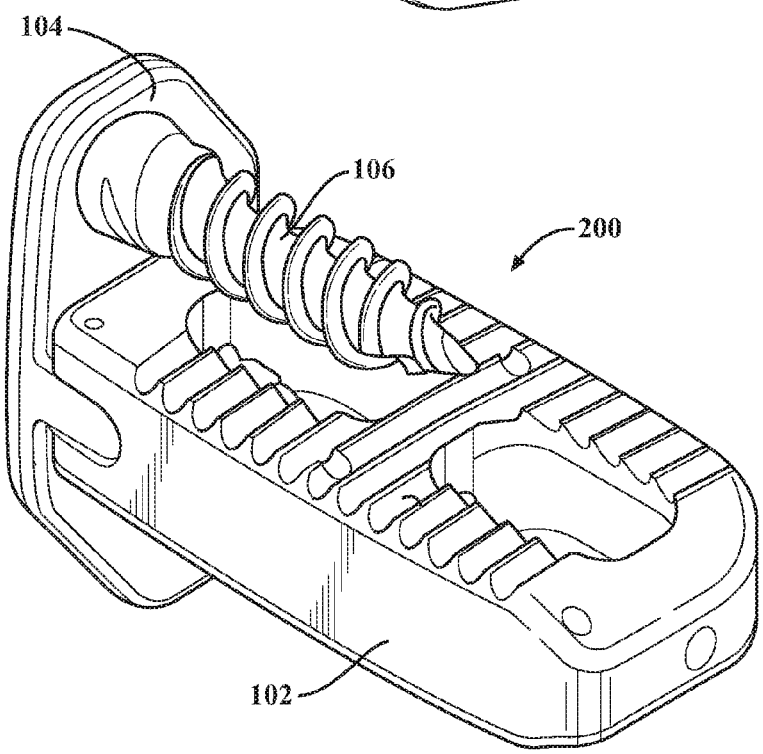
FIG. 2 is a perspective view of the implant of FIG. 1 looking in an opposite direction of FIG. 1.
Figure 3:
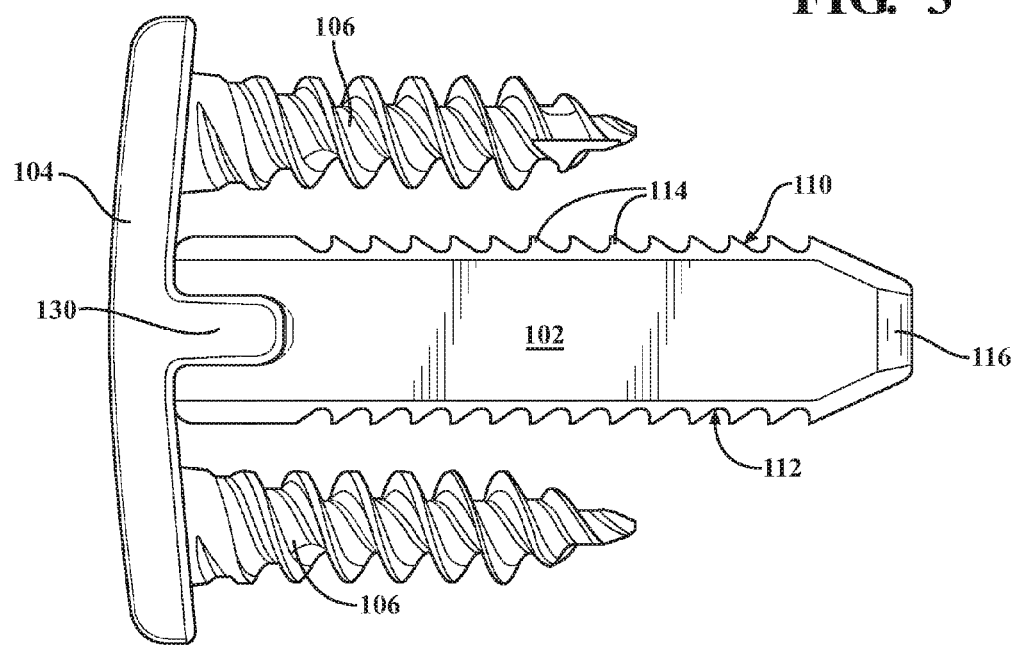
FIG. 3 is a side view of the implant illustrated in FIG. 1.
Figure 4:
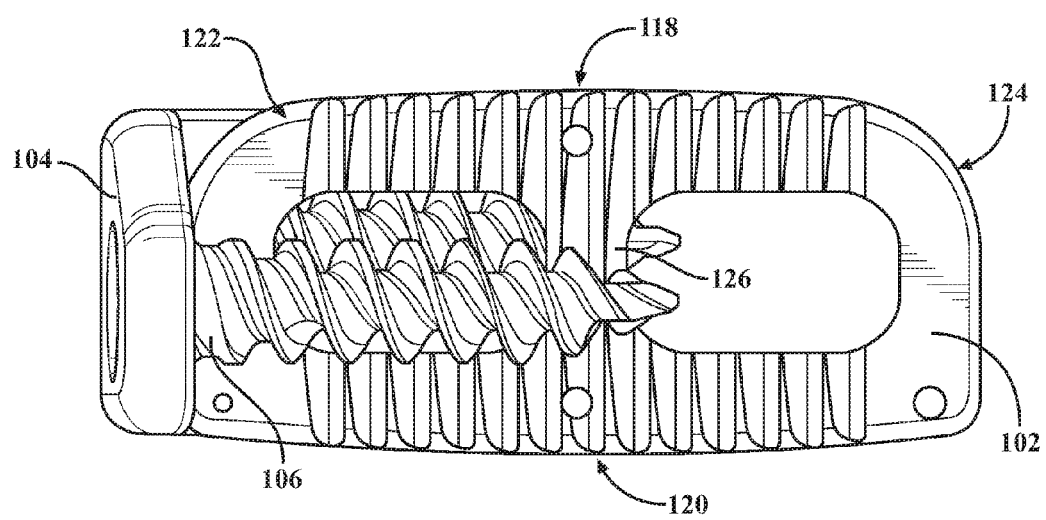
FIG. 4 is a view of the implant illustrated in FIG. 1 generally rotated 90 degrees about a longitudinal axis.
Figure 5:
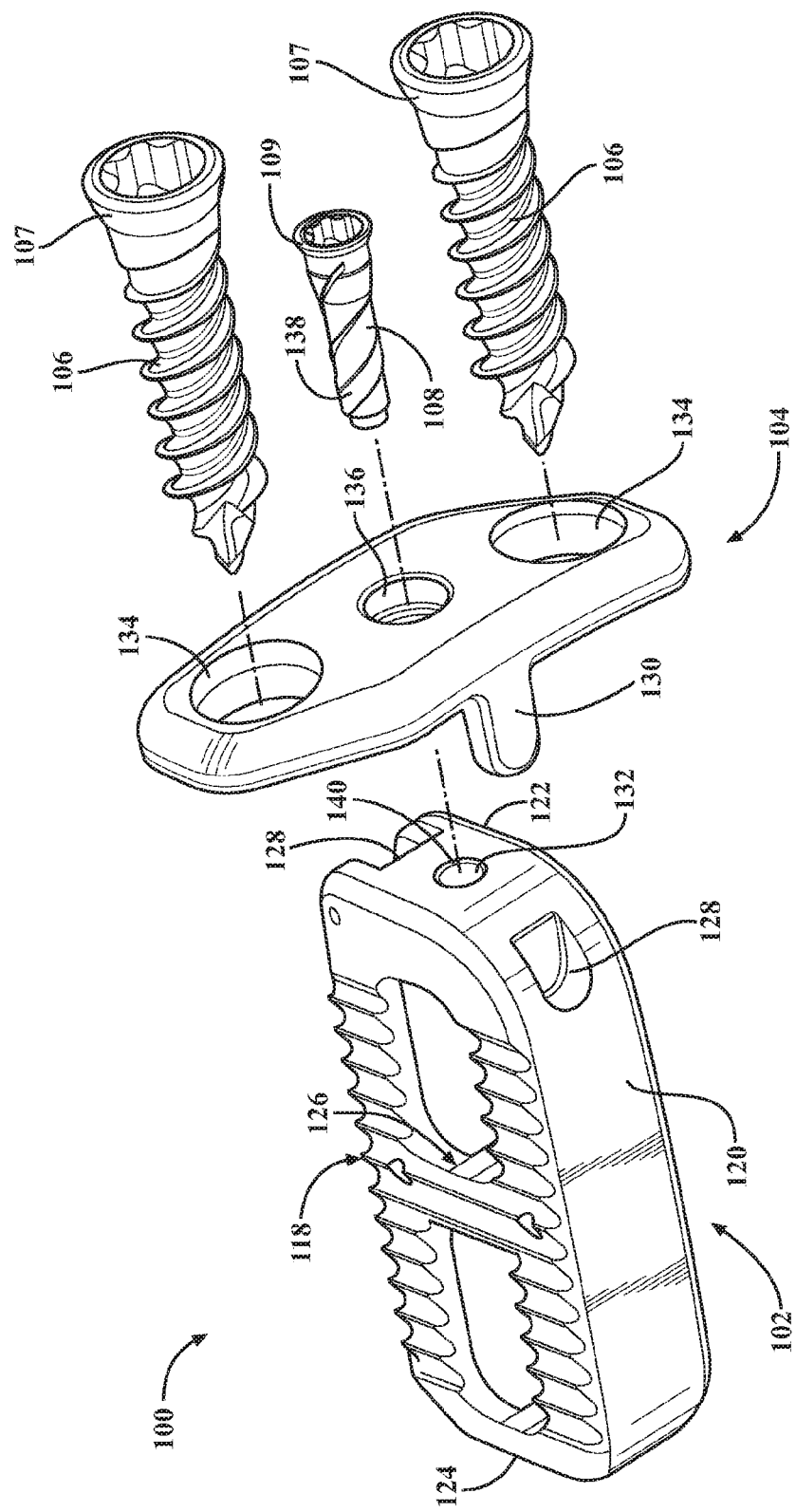
FIG. 5 is an exploded of the implant of FIG. 1 taken from the side.
Figure 6:
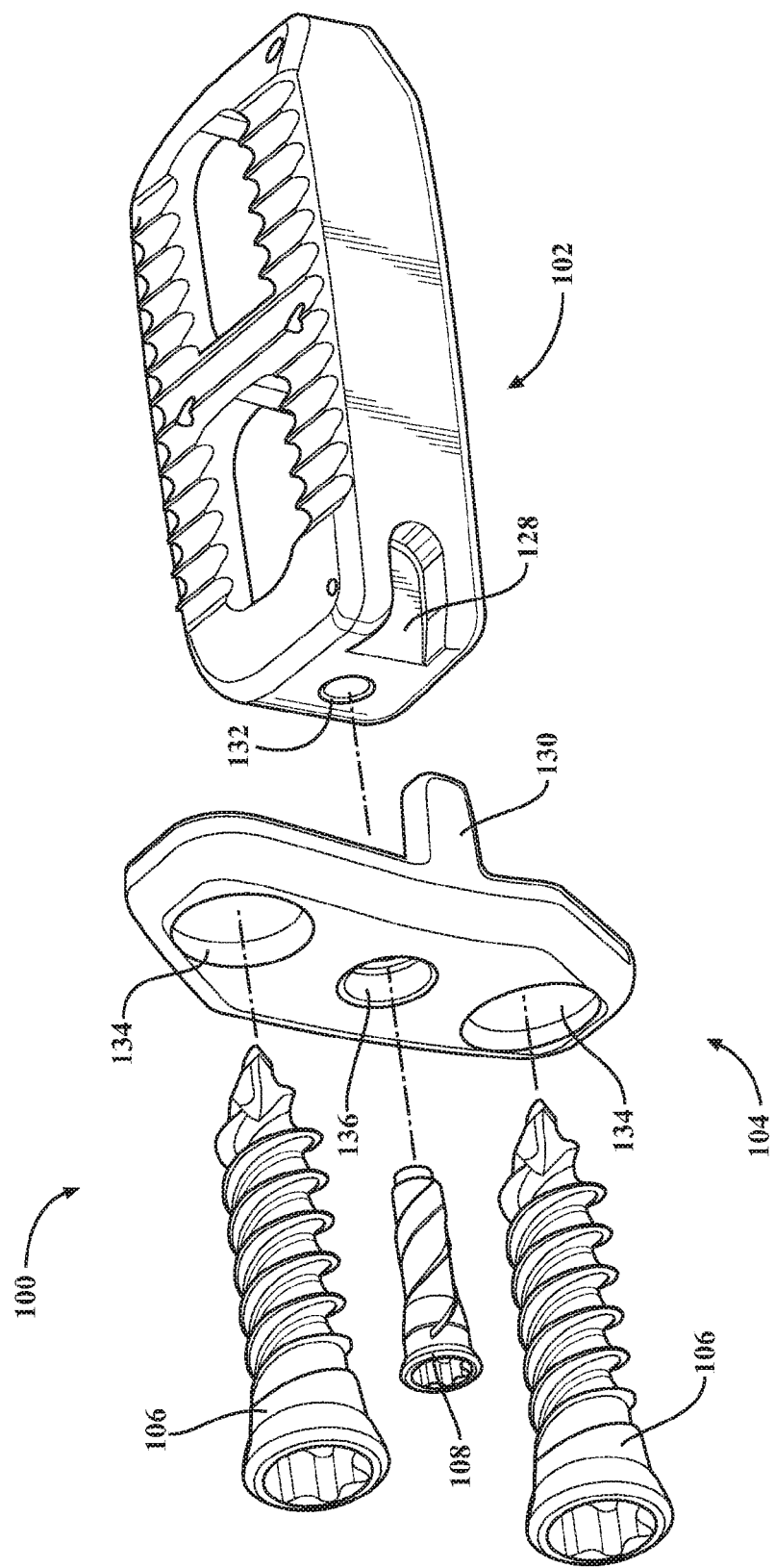
FIG. 6 is view FIG. 5 taken from the opposite side.
Figure 7:
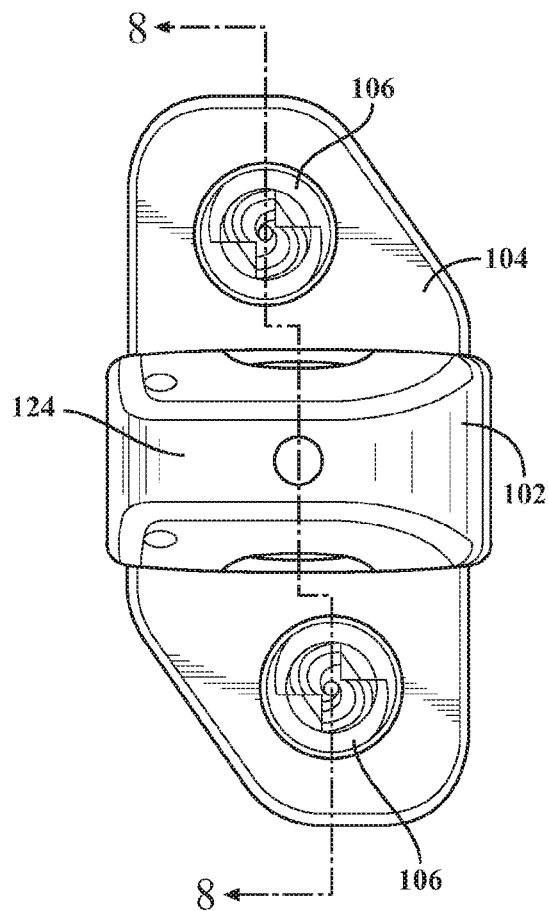
FIG. 7 is side view looking into a distal end of the implant of FIG. 1.
Figure 8:
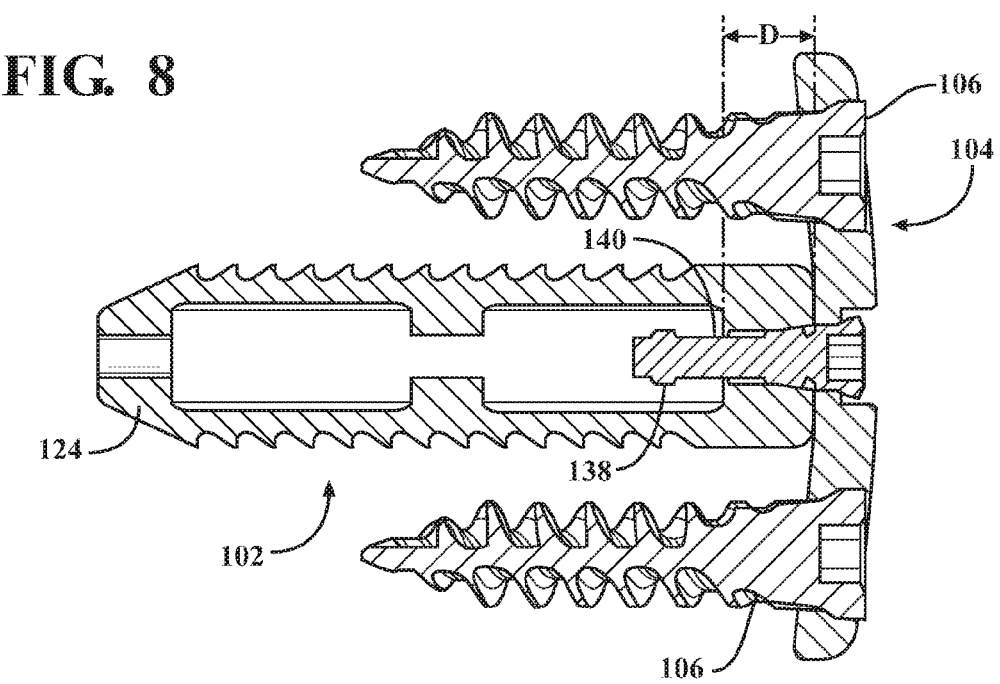
FIG. 8 is a cross-sectional view of the implant looking into a plane A of FIG. 7.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Referring to FIGS. 1-8, an exemplary implant 100 comprises a spacer 102, a plate 104, one or more temporary fixation screws 106, and an attachment member 108. The spacer 102 may be configured for insertion through a lateral or anterior aspect of the spine and into a disc space between two adjacent vertebrae. The spacer 102 may include various recesses and apertures for receiving mating features of the plate 104 and the attachment member 108. The fixation screws 106 may be used to attach the plate 104 to the two adjacent vertebrae.

During a lateral spinal fusion procedure, the spacer 102 may be inserted first into the patient through an opening in the side of the patient. For example, in a lumbar lateral interbody fusion (LLIF) procedure, the patient may be placed on his or her side while an opening is made from the side of the abdominal region to the spine. The spacer 102 may be compressed between the vertebrae providing some amount of force to restrain movement of the spacer 102. However, it typically is required by regulatory agencies that the spacer 102 be held in place by additional compressive forces applied by fixation structures such as rods, screws, and plates. In order to insert the fixation structures, the patient must be rotated from his or her side to the belly or the back side. During this rotation, the spacer 102 could become dislodged and migrate posteriorly towards the patient's spinal cord or anteriorly towards the patient's vascular structures. Accordingly, the plate 104 may be attached to the spacer 102 and adjacent vertebrae using the temporary fixation screws 106 and attachment member 108.

The spacer 102 may be formed by a sidewall that includes an anterior wall 118 and a posterior wall 120 which are coupled by a proximal side wall 122 and a distal side wall 124. A middle wall 126 may extend from the anterior wall 118 to the posterior wall 120 to provide additional reinforcement of the spacer 102 at a location about halfway between the proximal side wall 122 and the distal side wall 124. The spacer 102 includes a superior surface 110 and an inferior surface 112 for engagement with the adjacent vertebrae. Both the superior surface 110 and the inferior surface 112 may include teeth 114 or ridges to resist migration of the implant 100 laterally. At a distal end of the spacer 102, a bullet-nose 116 may ease insertion of the spacer 102 into the disc space.

The spacer 102 further includes recessed portions 128 extending partially through portions of the proximal side wall 122 and into the anterior wall 118 and posterior wall 120. The recessed portions 128 may include a profile configured to receive projections of an insertion instrument or a pair of projections 130 extending from the plate 104. The proximal side wall 122 also includes a first coupling aperture 132 configured to receive the attachment member 108.

The plate 104 includes attachment apertures 134 configured to receive the temporary fixation screws 106. The attachment apertures 134 may include diameters that are less than a diameter of a head portion 107 of the screws 106. In embodiments, attachment apertures 134 include a first attachment aperture and a second attachment aperture. The plate 104 includes the projections 130 which extend away from the plate 104 in the distal direction to engage with the recessed portions 128 of the spacer 102. The plate 104 includes a second coupling aperture 136 configured to receive the attachment member 108. The second coupling aperture 136 includes a diameter less than a diameter of a head portion 109 of the attachment member 108.

The attachment member 108 may include a thread 138 for engagement with a mating thread 140 of the spacer 102. Prior threaded attachment members for plates and spacers typically include screws with threads with a thread pitch typically less than a depth D of the threaded aperture in the spacer, sometimes by an order of at least three times and typically more on the order of six times such that at least six crests of the thread engage the spacer. Thus, the thread pitch is at most D/3 or more typically quite less and on the order of approximately D/6. It is appreciated that the term thread pitch used herein is defined as the distance between adjacent threads, e.g. the distance between the crest or root of two adjacent threads.

Referring now to FIGS. 11-14, the thread 138 of the present attachment member 108 may include a thread pitch TP that is significantly greater than prior thread pitches. For example, the thread 138 may include a thread pitch TP that is greater than one third of a depth D of the first coupling aperture 132 in the proximal wall 122 of the spacer 102. The thread 138 permits secure coupling of the spacer 102 with the plate 104 by about one half rotation of the attachment member 108 to engage less than one full crest of the thread 138.

Figure 14:
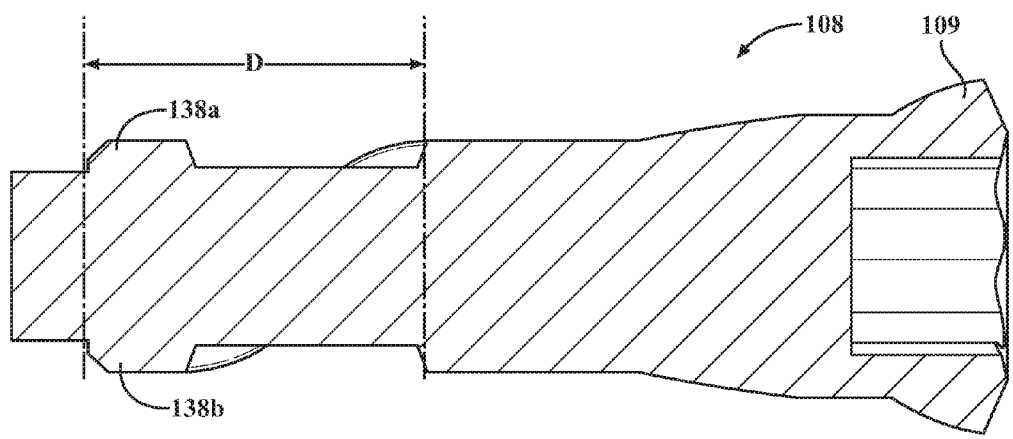
FIG. 14 is a cross-sectional view of the attachment member in plane B of FIG. 13.

In some examples, the thread 138 includes a long lead (pitch) trapezoidal form thread as seen in the cross-sectional view of FIG. 14. In some examples, the thread 138 includes a modified Acme thread. In some examples, the thread includes a first thread 138a and a second thread 138b with two separate leads forming a dual lead dual thread. In some examples, the thread 138 includes a double lead and a substantially steep thread pitch TP greater than or equal to approximately two times D where D is a depth of the first coupling aperture 132 (or a thickness of the proximal wall 122) of the spacer 102. In some examples, the thread 138 permits secure coupling of the spacer 102 with the plate 104 by about 180 degrees of rotation of the attachment member 108. For example, the plate 104 may be mounted onto the spacer 102 so as to register the second coupling aperture 136 with the first coupling aperture 132, inserting the attachment member 108 into the second coupling aperture 136 and rotating the attachment member 108 no more than half a turn.

Figure 9:
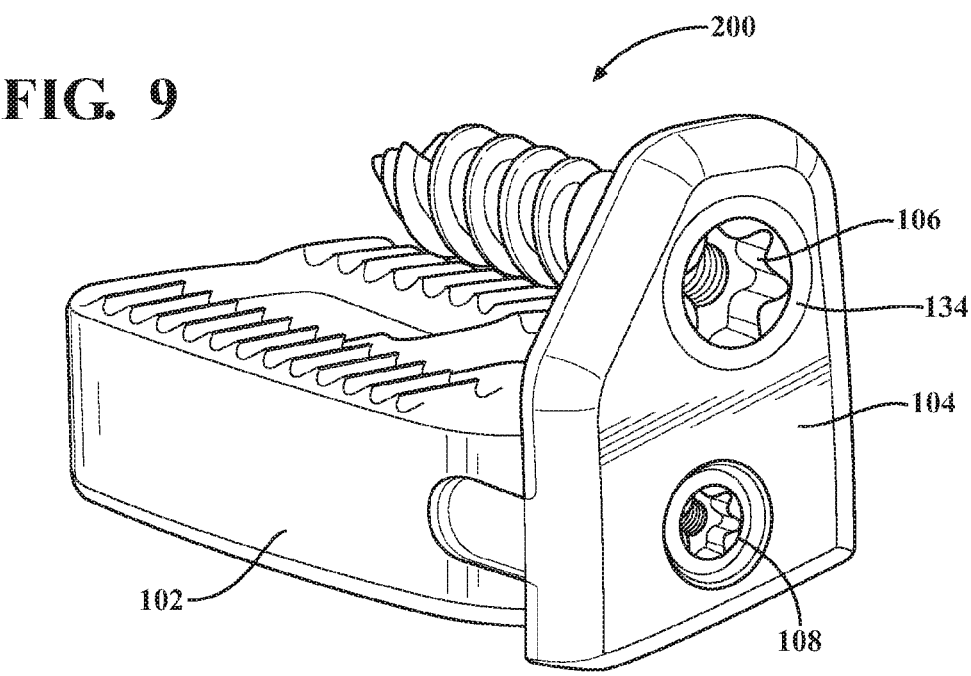
FIG. 9 is a perspective view of another exemplary implant according to the principles of the present disclosure.
Figure 10:
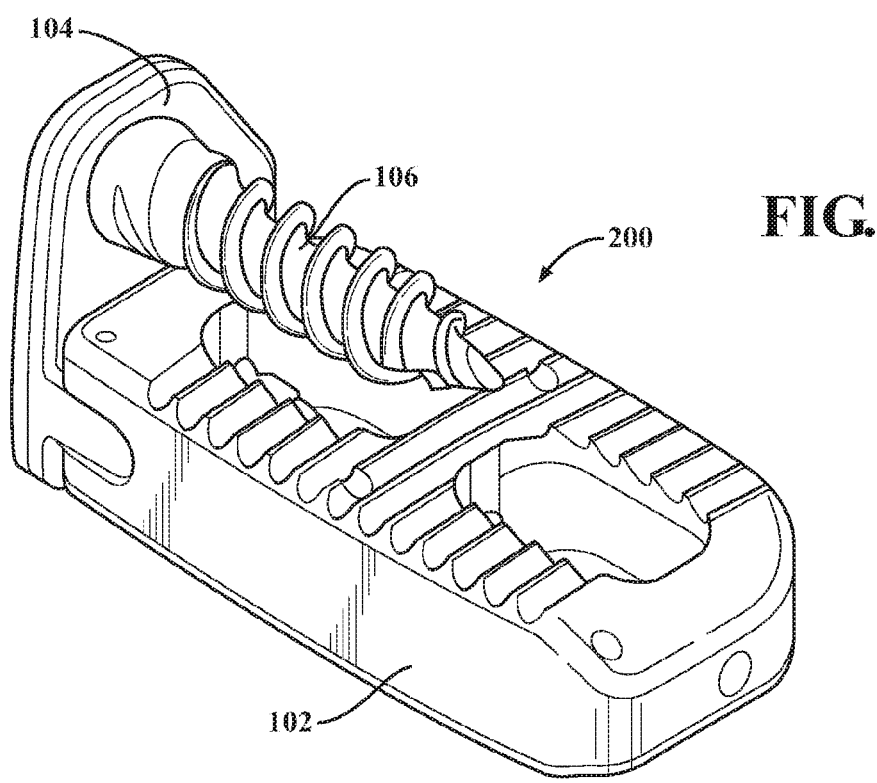
FIG. 10 is an isometric view of the implant of FIG. 9 looking in an opposite direction of FIG. 9.
Figure 11:
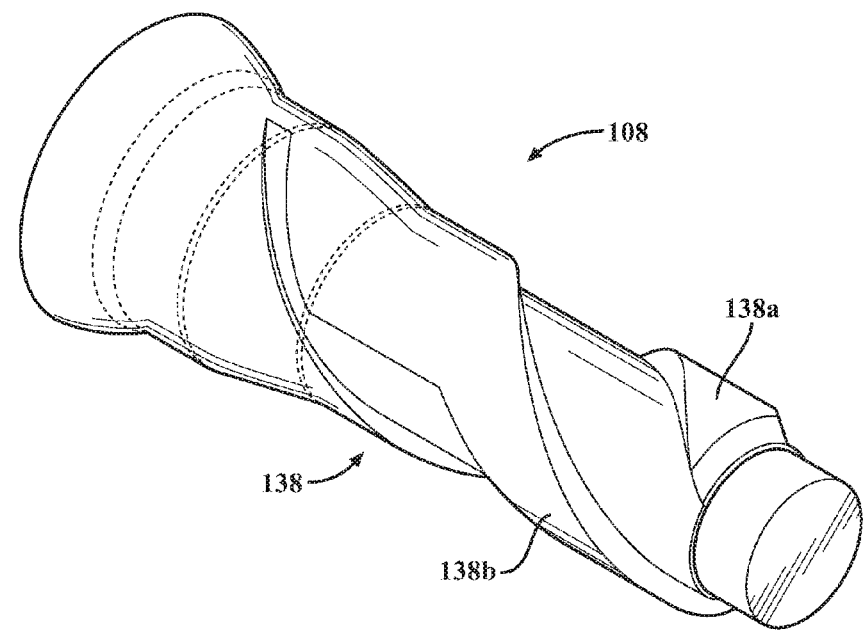
FIG. 11 is an illustrative view of an attachment member of the exemplary implant according to the principles of the present disclosure.
Figure 12:
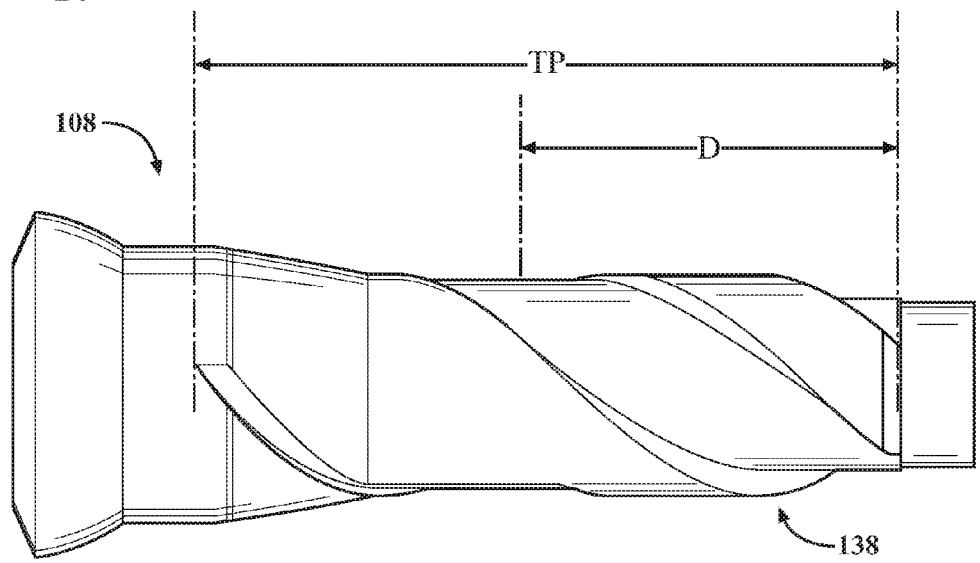
FIG. 12 is a side view of the attachment member shown in FIG. 11.
Figure 13:
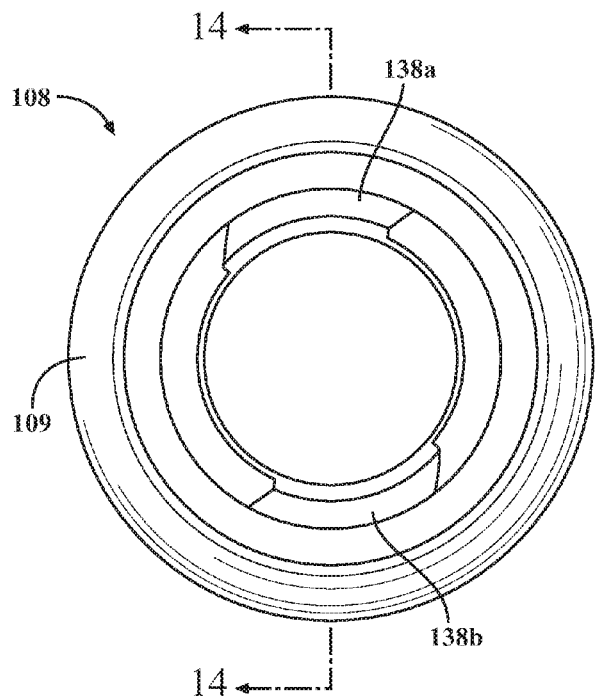
FIG. 13 illustrates a bottom view of the attachment member.

FIGS. 9-10 illustrate another exemplary implant 200 including the same or similar features as the first implant 100. However, in implant 200 a single attachment aperture 134 and a single temporary fixation screw 106 is provided. Otherwise, the same features are present as described above with reference to implant 100.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. A method for implanting an implant in a patient, wherein the implant is implanted between a pair of adjacent vertebrae, the method comprising the steps of:
providing a spacer having a first coupling aperture, the first coupling aperture having a first thread with a thread pitch that is greater than or equal to one third of a depth of the first coupling aperture;
providing a plate including a first attachment aperture and a second coupling aperture;
providing an attachment member including a mating thread that mates with the first thread;
inserting the spacer between the pair of adjacent vertebrae;
mounting the plate onto the spacer so as to register the second coupling aperture with the first coupling aperture; and
securing with no more than a half turn of the attachment member, the plate to the spacer wherein the mating thread of the attachment member works in concert with the first thread so as to be fully nested within the first coupling aperture.

2. The method of claim 1, further comprising the step of attaching a first temporary fixation screw to the first attachment aperture of the plate and driving the first temporary fixation screw into one of pair of adjacent vertebrae, and rolling the patient from their side to their belly or their back side.

3. The method of claim 1, wherein the thread pitch is greater than or equal to the depth of the first coupling aperture of the spacer.

4. The method of claim 1, further comprising the step of providing a second thread within the first coupling aperture, the second thread including a second thread pitch equal to the first thread pitch.

5. The method of claim 1, wherein the first thread comprises a long lead trapezoidal form thread.

6. The method of claim 1, wherein about one half rotation of the attachment member engages less than one full thread of the first thread with the first coupling aperture to couple the spacer with the plate.

7. The method of claim 1, wherein the plate includes a pair of projections extending distally in a fork formation to engage with a pair of recessed portions of the spacer.

8. The method of claim 1, wherein the spacer further comprises:
a distal end for insertion between two vertebrae;
a middle section including a pair of recessed portions on an outer surface of the middle section; and
a proximal end including the coupling aperture.

9. The method of claim 1, further comprising a second attachment aperture in the plate.

10. The method of claim 9, further comprising a second temporary fixation screw configured to attach the plate to a second vertebra when inserted through the second attachment aperture and driven into the second vertebra.

11. The method of claim 1, wherein the first thread includes a double lead and a thread pitch greater than or equal to approximately two times the depth of the first coupling aperture of the spacer.

* * * * *